United States Patent
Hibst

[19]

[11] Patent Number: 6,159,204
[45] Date of Patent: Dec. 12, 2000

[54] PULSED LIGHT SOURCE METHOD FOR CUTTING AWAY BIOLOGICAL TISSUE

[75] Inventor: Raimund Hibst, Erbach, Germany

[73] Assignee: Carl Baasel Lasertechnik GmbH, Germany

[21] Appl. No.: 08/973,691

[22] PCT Filed: Jun. 7, 1996

[86] PCT No.: PCT/EP96/02486

§ 371 Date: May 20, 1998

§ 102(e) Date: May 20, 1998

[87] PCT Pub. No.: WO96/41577

PCT Pub. Date: Dec. 27, 1996

[30] Foreign Application Priority Data

Jun. 8, 1995 [DE] Germany ............... 195 21 003

[51] Int. Cl.$^7$ ........................................... A61N 5/06
[52] U.S. Cl. ..................... 606/10; 606/3; 606/13
[58] Field of Search .................. 606/2, 3, 10–13

[56] References Cited

U.S. PATENT DOCUMENTS

| | | | |
|---|---|---|---|
| 4,672,969 | 6/1987 | Dew | 606/3 |
| 5,125,922 | 6/1992 | Dwyer et al. | 606/3 |
| 5,312,396 | 5/1994 | Feld et al. | 606/11 |

FOREIGN PATENT DOCUMENTS

| | | |
|---|---|---|
| 0164751 | 12/1985 | European Pat. Off. . |
| 3233671 | 3/1983 | Germany . |
| 3934646 | 4/1991 | Germany . |
| 4015066 | 11/1991 | Germany . |
| 92/18057 | 10/1992 | WIPO . |

OTHER PUBLICATIONS

Selective Photohermolysis: Precise Microsurgery by Selective Absorption of Pulsed radiation by Andersen et al; Science; vol. 220; Apr. 29, 1983 p. 524–7.

R. Hibst, et al., "Comparison of Different Mid–Infrared Lasers for the Ablation of Skin", Lasermedizin, vol. 11, 1995, pp. 19–26 No Translation.

*Primary Examiner*—David M. Shay
*Attorney, Agent, or Firm*—Ostrolenk, Faber, Gerb & Soffen, LLP

[57] ABSTRACT

A pulsed light source for cutting away biological tissue has a control unit that controls the light source in such a way that the light source supplies a series of pulses of predetermined duration and radiation intensity. The control unit may be operated to cause the light source to supply short pulses (10) at a predetermined and/or controllable rate of repetition with a radiation intensity sufficient to cut away the tissues, and radiation followed by light emission (11) or the like with a radiation intensity that is not sufficient to cut away the tissues but is sufficient to generate heat.

16 Claims, 3 Drawing Sheets

PULSED LIGHT SOURCE METHOD FOR CUTTING AWAY BIOLOGICAL TISSUE

BACKGROUND OF THE INVENTION

The invention relates to a pulsed light source for removing biological tissue and particularly to controlling the light source for removing tissue or warming the irradiated area.

It is known from many medical applications that tissue can be removed or cut with the aid of adequately intensive light, in particular laser radiation. Removal is accompanied by heating of the surrounding tissue. The extent of this heating is determined in particular by the wavelength of the radiation used, or the coefficient of absorption of the tissue dependent on the latter, and by the irradiation intensity. In the case of high absorption in the tissue and low irradiation intensity, as is the case for example with a $CO_2$ continuous-wave laser, tissue is pyrolytically vaporized with a relatively great thermal side effect. In a typical case, the crater or cut formed in soft tissue is surrounded by a carbonization layer, a zone broken up by vacuoles, a coagulation zone and a reversibly thermally damaged region. The coagulation of the tissue produced by the heating, and the accompanying hemostasis is of practical advantage in many cases, because it makes possible cuts which do not bleed. On the other hand, for applications in which as little damage as possible to the remaining tissue and good healing of the wound are important, great thermal effects are disadvantageous. Carbonization of the tissue surface, as occurs when cutting with continuous-wave lasers, is likewise unfavorable. It has already been attempted in the case of such lasers to reduce the thermal damage by increasing the irradiation intensity while at the same time shortening the time period in which it acts.

On the other hand, research in recent years has shown that, with pulsed light sources of high power and a wavelength in the ultraviolet or infrared ranges, for example TEA-$CO_2$, Er:YAG, Er:YSGG or excimer lasers, hard or soft tissue can be removed without carbonization and with only little thermal damage by a very effective thermomechanical ablation process. For instance, in the case of soft tissue, the marginal edge which coagulated after use of the free-running Er:YAG laser in vivo is only about 30–40 $\mu$m. This is of particular interest for the treatment of superficial skin lesions or for cosmetic surgery, because damage of the tissue beyond that which is removed is largely avoided. If, however, the capillary layer of the tissue is reached, the removal is stopped by emerging blood.

In all the surgical applications of light sources used thus far, the removal properties and the thermal side effects are coupled in as much as precise removal with high removal efficiency is always accompanied by a small thermal side effect, and vice versa. A known possible way of achieving different thermal side effects is that of combining a plurality of light sources of different wavelengths in one device. However, the parallel operation of the two light sources required for simultaneous cutting and coagulating requires high expenditure on apparatus.

DE 39 34 646 A1 discloses a method and an apparatus of the type stated at the beginning in which a specifically directed vaporization without partial decomposition or burning is to be achieved by the luminous effect occurring in the pyrolysis process being used as a control signal for the control unit. By this means, the control unit is controlled in such a way that either the laser power, the clock ratio or the pulse energy are changed.

Furthermore, DE 32 33 671 A1 discloses a laser apparatus having a memory means for storing a multiplicity of data records, which specify parameters for the operating conditions for a particular laser radiation. Details on the individual parameters, and consequently an optimum removal of tissue, are not specified here however.

SUMMARY OF THE INVENTION

The invention is based on the object of providing a pulsed light source of the type stated at the beginning which makes it possible with only a single wavelength to remove tissue precisely and at the same time with little thermal side effects and also without carbonization of the surface and, independently of the removal, to heat the tissue in a specifically directed and controllable manner, in order for example to produce a coagulation zone specific for the intended use.

A biological tissue irradiating light source is activated to supply first irradiation of an intensity to remove biological tissue and then second irradiation of an intensity insufficient to remove tissue, but sufficient to produce a thermal effect in the tissue. Pulsing and duration of pulses are as disclosed in detail below.

DETAILED DESCRIPTION OF THE INVENTION

Figure 1:
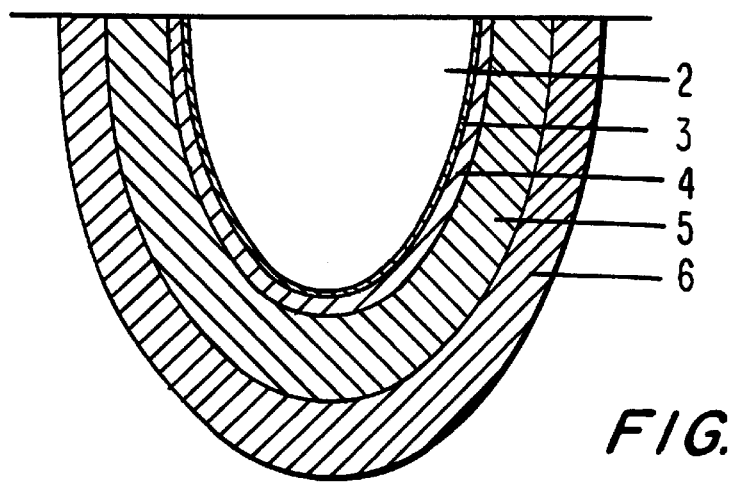

With the pulsed light source according to the invention, biological tissue can be removed precisely and with little thermal side effects and in addition can be heated to a variable extent.

The light emission of the light source according to the invention is modulated in a controllable manner in such a way that, within a pulse cycle, a high-power radiation pulse used for tissue removal is followed in a defined time by a light radiation with reduced irradiation intensity, which may have the form of a reduced-power end portion of the radiation pulse or the form of a series of pulses comprising one or more radiation pulses of which the power or energy content is not sufficient for tissue removal and consequently leads only to the tissue being heated.

The pulsed light source according to the invention allows a hitherto unknown range of surgical applications in which a single radiation source can be used with little expenditure on apparatus, ranging from precision surgery with little thermal damage in areas which are not perfused with blood, or only to a slight extent, through to the removal of blood-perfused tissue with hemostasis. Since the thermal side effect, and consequently the thickness of the coagulation zone, can be adapted to the individual intervention, in any case a just sufficient and at the same time minimally damaging thermal necrosis zone can be produced. In addition, such an enlarged coagulation zone does not lead to any sacrifices in the quality of the cut.

The light source according to the invention is preferably an ultraviolet or infrared light source.

The first radiation pulse of the pulse cycle corresponds to the radiation emission as commonly used for the ablation of biological tissue with little damage. The tissue removal commences when a specific amount of energy per element of volume $H_{abl}$, dependent on the type of tissue and on the irradiation intensity, has accumulated on its surface. This corresponds to a threshold value of the irradiation ($F_S$), which is likewise dependent on the tissue and the irradiation parameters. Part of the irradiated energy remains in the tissue at the end of the pulse, heats the marginal region of the craters or cuts and leads to the thermal side effects described, in particular the coagulation of the tissue.

According to a preferred refinement of the invention, the parameters of the first radiation pulse of the series of pulses is chosen such that the heating and tissue damage produced in connection with the tissue removal is low. This is achieved by the combination of high irradiation intensity and high absorption in the tissue (typical coefficient of absorption greater than 10 cm$^{-1}$).

The light source used for this is preferably a pulsed Er:YAG, Er:YSGG, Ho:YAG, Tm:YAG, CO, $CO_2$ or excimer laser.

Some data on this can be taken from the publication by R. Hibst and R. Kaufmann, 'Vergleich verschiedener Mittelinfrarot-Laser für die Ablation der Haut' [Comparison of various mid-infrared lasers for ablation of the skin], Lasermedizin [Laser Medicine], Vol. 11 (1995), pages 19–26.

Typical values for the Er:YAG laser are:

energy required for removal per element of volume $H_{abl}$= 1.5 kJcm$^{-3}$ threshold value of the irradiation intensity about 1 Jcm$^{-2}$ pulse duration in the range from 150 to 600 µs irradiation in clinical use on the skin about 5–20 Jcm$^{-2}$ average irradiation intensity several 10 kWcm$^{-2}$ if removal is over a surface area, size of the spot 1 to 3 mm in diameter The laser-related power is calculated from the irradiation intensity and the size of the spot.

The coagulation zone caused by the removing pulse is enlarged according to the invention by emitting after the short pulse leading to removal a respectively following light radiation with an irradiation intensity and/or irradiation which is not sufficient for the removal of tissue but produces a thermal effect.

This subsequent light radiation in the form of a pulse end portion of reduced irradiation intensity or of at least one, but preferably more than one light pulses is dimensioned with regard to its power or energy such that, given a predetermined size of the irradiation zone, the removal threshold value of the tissue is not reached.

According to a refinement of the invention, at least one pulse with low irradiation intensity is used for this. In order that the tissue is not removed and is only heated, pulses with such a low irradiation intensity that, as a result of the heat conduction, the energy per element of volume accumulated at the surface remains below $H_{abl}$, i.e. the irradiation intensity remains below the threshold value required for removal.

To estimate the upper limit of the irradiation intensity, it may be assumed that the energy H occurring per element of volume results from the supply of energy produced by light absorption and an energy loss proportional to H:

$$\frac{dH}{dt} = \mu \cdot I_0 - \frac{1}{\tau} \cdot H$$

($I_0$: irradiation intensity, $\mu$: coefficient of absorption).

The thermal relaxation time $\tau$ used as the proportionality factor for the rate of loss can be estimated from the known formulae. It decreases quadratically with the heated volume, and therefore with increasing $\mu$. The threshold value of the irradiation intensity $I_S$ is reached when, in the state of equilibrium (dH/dt=0), the energy density at the surface is equal to $H_{abl}$. It thus follows from the above equation that:

$$I_S = \frac{H_{abl}}{\mu \cdot \tau}$$

For the Er:YAG laser, the thermal relaxation time of the tissue can be estimated as a few µs for the beginning of the irradiation, so that the remaining values (see above) give an irradiation intensity $I_S$ in the kWcm$^{-2}$ range. With increasing enlargement of the heated region, $I_S$ then decreases. The exact progression is difficult to calculate here. For a layer of a thickness of, for example, 80 µm, the thermal relaxation time is about 30 ms, which leads to a maximum permissible irradiation intensity of about 5 Wcm$^{-2}$. An advantageous refinement of this alternative is therefore a progression with decreasing irradiation intensity. The irradiation intensity (power) and the duration of the pulse then determines the extent of heating.

If the required difference in the irradiation intensity between the removing pulses and the heating pulses is technically difficult to accomplish in the case of a given laser, according to a further refinement of the invention it is envisaged to use a sequence of pulses with an energy content below the removal threshold value.

As a point of reference for this threshold value, the threshold values $F_S$ (see above) determined from the removal measurements may be used. The threshold values increase with decreasing irradiation intensity (they are theoretically infinite at an irradiation intensity of $I_S$) and decrease in the case of preheated tissue. Thus, for the Er:YAG laser, initially $F_S$=1 Jcm$^{-2}$ would be assumed and, in an experimental situation, the irradiation intensity of each individual pulse or its duration would be changed such that removal no longer quite takes place. The individual factors, irradiation intensity and pulse duration, are governed by the technical requirements of the light source; primarily decisive for the effect is their product.

According to one embodiment, the irradiation intensity and the duration of the pulses following the first radiation pulse may vary from one another. This is appropriate, for example, for the Er:YAG laser if, for supplying the pumping flashlamp of this laser, the energy of a single capacitor bank is used for generating the entire series of pulses. The decreasing voltage causes the laser pulses to be increasingly weak, which however can be compensated by a correspondingly prolonged pulse duration.

The optimum time interval between the subpulses or between the removing pulse and the series of pulses for heating results from the thermal relaxation time of the tissue surface. To be able to introduce as much energy as possible into the tissue without removing it, it is favorable to allow the tissue surface to cool between two such pulses with respect to the temperature leading to removal. In order at the same time to produce a great depth of the coagulation, this cooling should not proceed right down to the (physiological) starting temperature (typically 37° C.). Rather, the subsequent heating by the following pulse should take place at the latest when the surface has reached the temperature required for the desired coagulation, of about 60° C. to 70° C. This time period increases with the optical depth of penetration of the radiation used.

In addition, the cooling behavior of the surface depends on its prehistory. In the case of the first laser pulse, the superficial heating of the tissue leads to a very steep temperature gradient with a correspondingly rapid falling of the temperature, caused by the heat conduction. The heat conduction also causes layers of tissue below the surface to be heated, so that the temperature gradient for a subsequent heating pulse is smaller. The increase in the thermal relaxation time with the number of heating pulses can be seen from a measurement of the surface temperature. An optimized sequence of heating pulses will therefore generally have different time intervals between the individual pulses. By analogy, the energy content of the individual pulses will be different.

Model calculations and measurements show for the Er:YAG laser that the temperature increase required for a coagulation of the skin in vivo from 30 K to 40 K is reached again at the surface a few ms after the end of the pulse. For the Ho:YAG laser, about 20 times this value can be expected. The exact times are to be determined experimentally in each case for the tissue under consideration and the wavelength used.

For effects other than coagulation, for example hyperthermia, other temperatures and times which can be readily determined by a person skilled in the art are of course critical.

In the case of this embodiment of the series of pulses used for heating, the energy introduced altogether (per element of surface) into the tissue, and consequently the depth of coagulation, can be advantageously controlled by the number of pulses in the series of pulses following the first pulse.

In the case of a modified embodiment, as an alternative to the predetermination of fixed parameters for the individual heating pulses, a control of the pulse energy levels, durations and interpulse periods on the basis of the surface temperature measured continuously or intermittently can be used. As soon as the surface temperature drops below a predetermined minimum value (for example 70° C.), the laser is activated. The laser emission is stopped again when the preset upper limit value (for example 200° C.) is reached.

In the case of this way of accomplishing the series of pulses used for heating, the energy introduced altogether (per element of surface) into the tissue, and consequently the depth of coagulation, can be advantageously controlled by the number of pulses in the series of pulses following the first pulse.

Of course, the optimized series of heating pulses may also be used without the removing pulse for coagulating. Similarly, it may be advantageous to apply the heating pulses before the removing pulse (as well), if, for example, infected tissue is to be killed off before the removal, which is accompanied by a dispersion of tissue fragments.

BRIEF DESCRIPTION OF THE INVENTION

Figure 2:
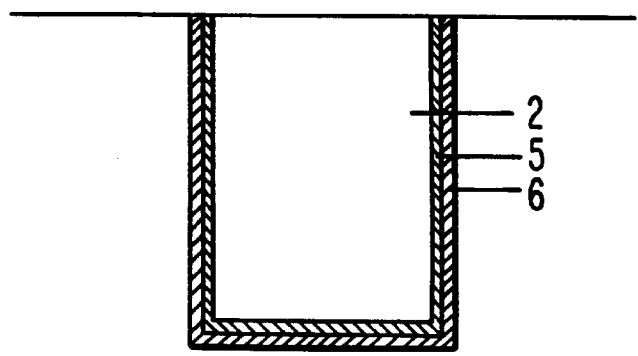
Figure 3:
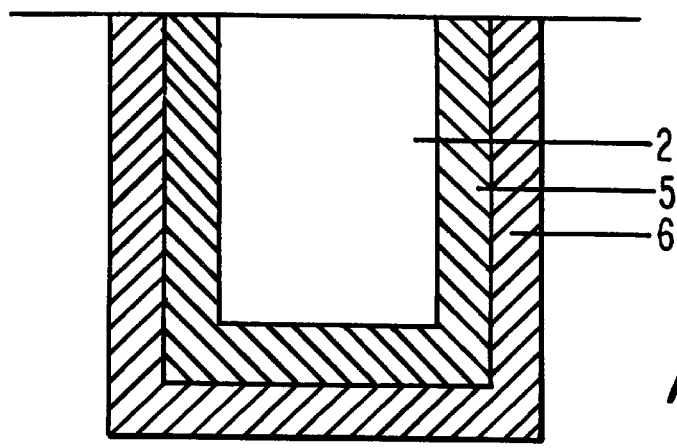
Figure 4:
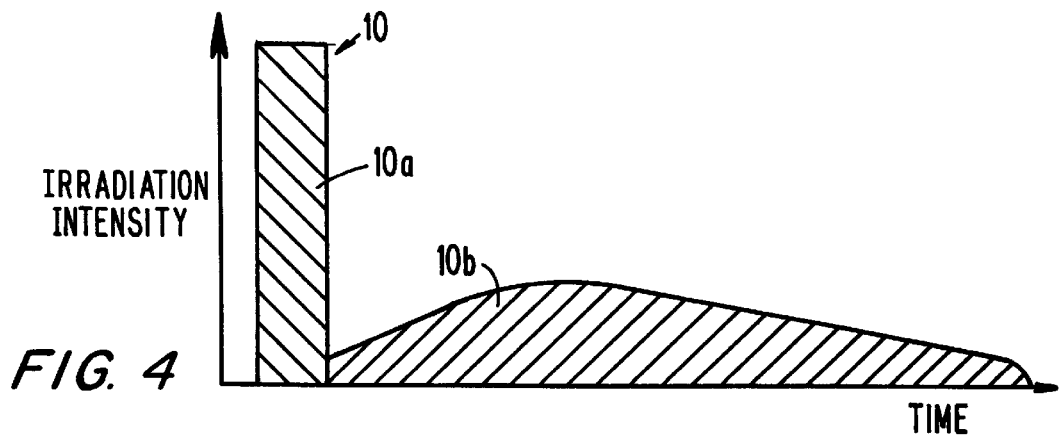
Figure 5:
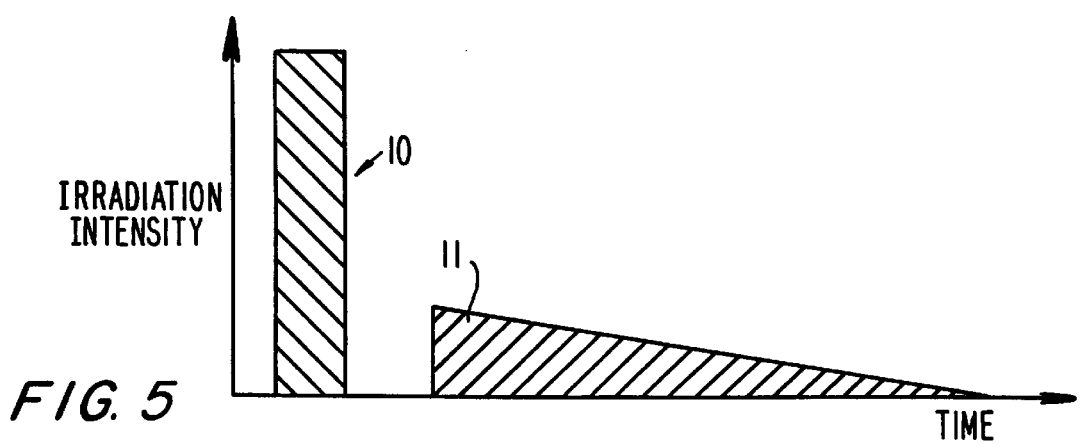
Figure 6:
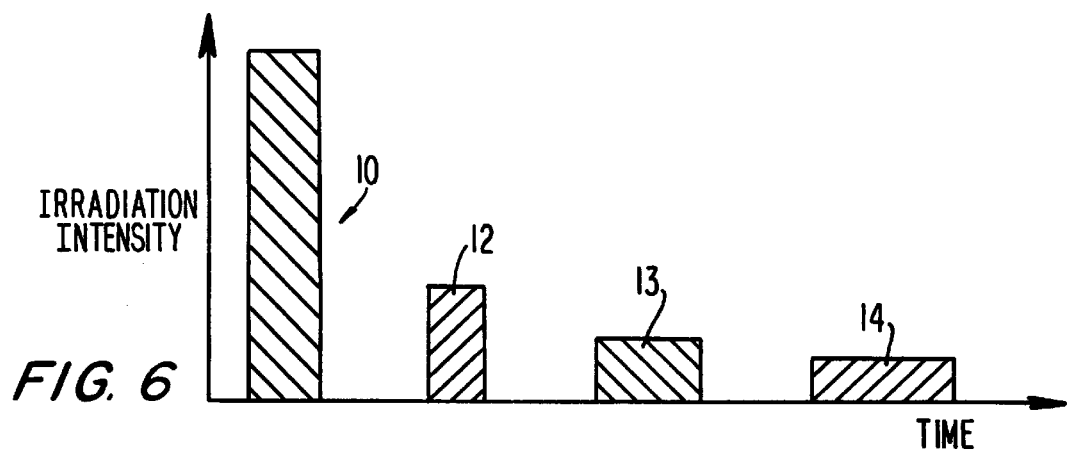
Figure 7:
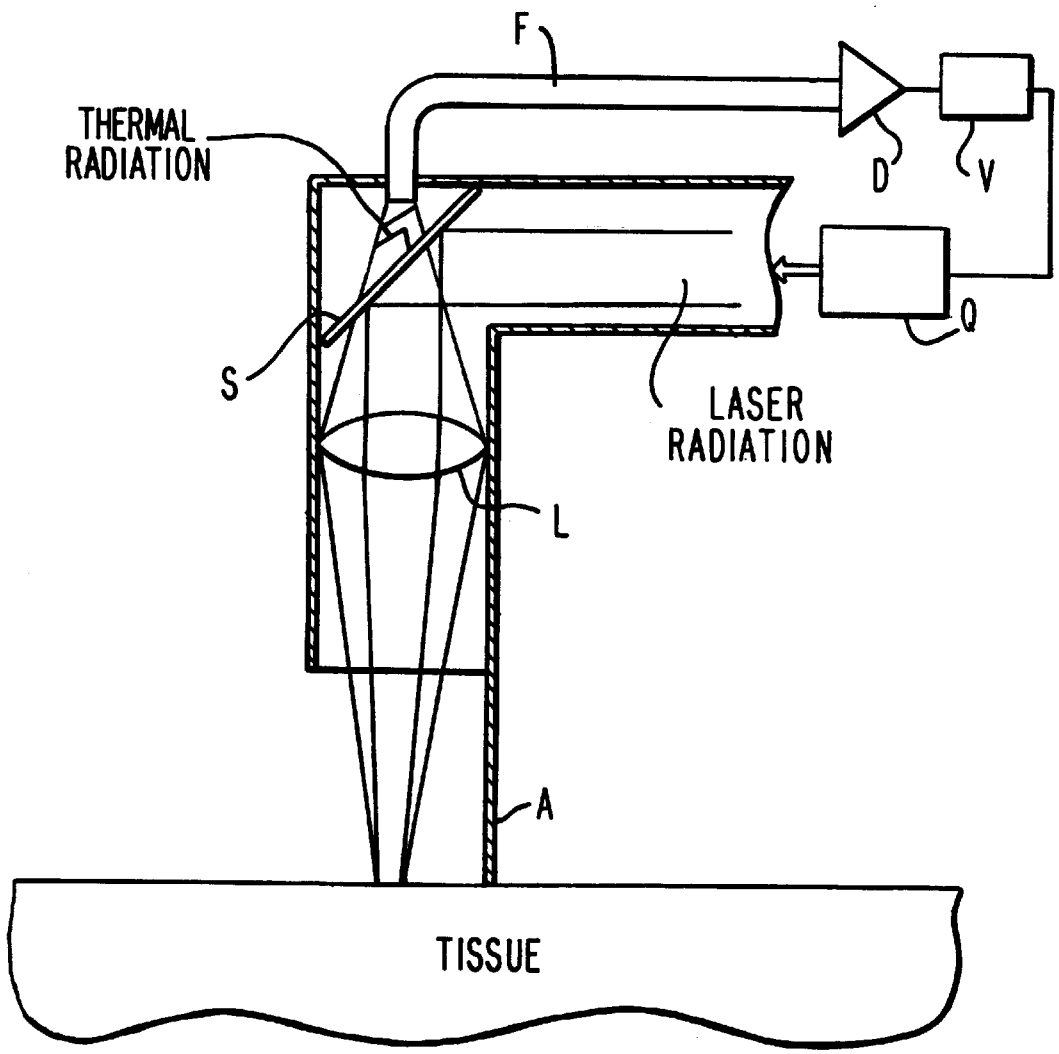

The invention is explained in more detail below with reference to the drawings, in which:

FIG. 1 shows a section through a region of tissue after irradiation in the case of high tissue absorption and low irradiation intensity, FIG. 2 shows a section through a region of tissue after irradiation in the case of high tissue absorption and high irradiation intensity, FIG. 3 shows a section through a region of tissue after irradiation with a pulsed light source according to the invention, FIG. 4 shows a first embodiment of a pulse which has a beginning-of-pulse portion, inducing removal, and an end-of-pulse portion, following the first, with reduced irradiation intensity, FIG. 5 shows a preferred embodiment of a sequence of pulses with a first pulse, inducing removal, and a pulse following the latter with decreasing irradiation intensity, FIG. 6 shows a further embodiment of a sequence of pulses with a first pulse, inducing removal, and a series of pulses following the latter with increasingly weaker, but correspondingly prolonged pulses, FIG. 7 shows a configuration of an apparatus with a control of the laser in dependence on the surface temperature of the tissue.

DESCRIPTION OF PREFERRED EMBODIMENTS

In FIG. 1 there is shown a section through a region of tissue as obtained, for example, in the case of high absorption in the tissue and low irradiation intensity. This occurs, for example, in the case of the $CO_2$ continuous-wave laser, which is directed at the tissue surface 1. The crater or cut 2 formed in the tissue is surrounded by a carbonization zone 3, a zone 4 broken up by vacuoles, a coagulation zone 5 and a reversibly thermally damaged region 6. The coagulation of the tissue produced by the heating and the accompanying hemostasis is of practical advantage in many cases, because it makes possible cuts which do not bleed. For applications in which as little damage as possible to the remaining tissue and good healing of the wound are important, great thermal effects are disadvantageous. Carbonization of the tissue surface is likewise unfavorable.

In FIG. 2 there is shown a section corresponding to FIG. 1, which shows the irradiation of a pulsed light source of high power and a wavelength in the ultraviolet or infrared range. Examples of such a light source are TEA-$CO_2$, Er:YAG, Er:YSGG or excimer lasers. With these lasers, hard or soft tissue can be removed without carbonization and with only little thermal damage by a very effective thermomechanical ablation process. The zone 5 which, in the case of soft tissue, coagulated after use of the free-running Er:YAG laser has in vivo only a thickness of about 30–40 $\mu$m. This is of particular interest for the treatment of superficial skin lesions or for cosmetic surgery, because damage of the tissue beyond that which is removed is largely avoided. If, however, the capillary layer is reached, the removal is stopped by emerging blood.

FIG. 3 shows a section corresponding to FIGS. 1 and 2 through a tissue after irradiation with the pulsed light source according to the invention. As will be explained in more detail below with reference to FIGS. 4 and 5, in this case the light emission of a pulsed ultraviolet or infrared light source is modulated in a controllable manner in such a way that, within a pulse cycle, a high-power pulse sufficient for tissue removal is followed in a defined time by a series of pulses comprising one or more pulses of which the power or energy content is not sufficient for tissue removal and consequently leads only to the tissue being heated. In this case, the crater 2 is surrounded by a coagulation zone 5 of controllable size. In this way, it is possible to remove tissue precisely and at the same time with little thermal side effects and without carbonization of the surface and, independently of the removal, can be heated in a specifically directed and controllable manner.

FIG. 4 shows a first embodiment of a pulse for achieving the removal shown in FIG. 3. In this case, each pulse comprises a short, first beginning-of-pulse portion 10, sufficient for removal, and a subsequent end-of-pulse portion of reduced irradiation intensity. With regard to the individual parameters of the pulse portions, reference is made to the discussion above.

FIG. 5 shows a second embodiment of a sequence of pulses for achieving the removal shown in FIG. 3. In this case, in a pulse cycle, a first, short pulse 10, sufficient for removal, is followed by at least one further pulse 11, which is separated from the pulse 10 by a time interval, has an irradiation intensity decreasing over time and merely produces a heating effect.

In FIG. 6 there is shown a further embodiment of a sequence of pulses in which, in a pulse cycle, the short pulse 10 of high irradiation intensity, sufficient for removal, is followed by a sequence of pulses 12 to 14 of which the irradiation intensity decreases in each case, but the duration of which increases.

Of course, the irradiation intensity of the pulses 11, or 12 to 14, following the first pulse 10 and their duration could also be constant, as long as they do not lead to further damage or removal of the tissue. Furthermore, the number of these pulses 12 to 14 may be selected according to the purpose in question on the basis of the criteria stated at the beginning for the respective application.

An alternative to the predetermination of fixed parameters for the individual heating pulses is the control of the pulse energy levels, durations and interpulse periods on the basis of the surface temperature measured continuously or intermittently, for example between the individual pulses. As soon as the surface temperature drops below a predetermined minimum value (for example 70° C.), the laser is activated. The laser emission is stopped again when the preset upper limit value (for example 200° C.) is reached.

A possible refinement of such an apparatus in the form of a hand-held appliance is diagrammatically shown in FIG. 7. The laser radiation from a laser source Q is deflected by means of a beam-splitting mirror S, which is transmissive to thermal radiation, and is focussed on the tissue by a lens L which is transparent to laser radiation and thermal radiation. The irradiated surface region of the tissue is likewise projected through the lens L onto the end face of a light-conducting fiber transmitting the thermal radiation (for example a silver halide fiber or chalcogenide fiber). This fiber conducts the thermal radiation to an infrared detector D. From the output signal of the latter, which is amplified in an amplifier V, after appropriate calibration the surface temperature of the tissue being worked at the time can be calculated, and this can then be used for the described control of the laser.

In the case of this embodiment of the series of pulses used for heating, the energy introduced into the tissue altogether (per element of surface), and consequently the depth of coagulation, can be advantageously controlled by the number of pulses in the series of pulses following the first pulse.

Although only laser light sources have been mentioned above as examples of the light source, these examples are in no way restrictive, since other light sources, the light generating process of which is not based on the laser principle, with a corresponding wavelength and irradiation intensity may also be used, such as for example pulsed high-pressure gas discharge lamps with xenon or other gas filling.

What is claimed is:

1. A method for removing biological tissue by irradiation from a light source which is selectively activated for applying its output light to said biological tissue, the method comprising the steps of:
controlling the activation of said light source for selectively supplying a pulse of a first irradiation of an intensity sufficient for removing biological tissue with a small thermal effect in the tissue irradiated; and
following said pulse with at least one pulse of a second irradiation of an intensity not sufficient for removing biological tissue but sufficient to produce a large thermal effect in the tissue irradiated:
wherein the pulses have substantially the same wavelength.

2. The method of claim 1, further comprising spacing one pulse from another pulse based on a surface temperature of the tissue irradiated.

3. The method of claim 1, wherein the light source emits light having high absorption in the tissue.

4. The method of claim 1, wherein the second irradiation subsequent to a respective pulse of said first irradiation is provided in a second pulse portion of reduced intensity for only heating the tissue during said second pulse portion.

5. The method of claim 4, further comprising dimensioning the second pulse portion such that over a predetermined size of the irradiation zone, the removal threshold of the biological tissue is not reached.

6. The method of claim 4, wherein the light source is activated such that the second pulse portion is comprised of at least one second pulse and the at least one second pulse has an irradiation intensity that decreases over time.

7. The method of claim 4, further comprising activating the light source such that the second pulse portion is comprised of at least one second pulse and the at least one second pulse initially has an irradiation intensity that increases over time and then subsequently decreases over time.

8. The method of claim 4, wherein the light source is activated such that the second pulse portion comprises a sequence of second pulses and each successive second pulse has a decreasing irradiation intensity but an increasing pulse duration, and for a predetermined size irradiation zone, the energy of each of the second pulses is below the biological tissue removal threshold value.

9. A method of claim 1, wherein said first irradiation is provided by a respective first pulse portion of sufficient duration and intensity in the range of from 1 to 250 $Jcm^{-2}$ per pulse so as to remove tissue with little damage and with only coagulation of marginal regions of tissue removal.

10. The method of claim 9, wherein said first pulse portion has a power of more than 500 watts and a duration of 50 to 1000 microseconds.

11. The method of claim 9, wherein the second irradiation subsequent to a respective pulse of said first irradiation is provided in a second pulse portion of reduced intensity for only heating the tissue during said second pulse portion.

12. The method of claim 11, further comprising dimensioning the second pulse portion such that over a predetermined size of the irradiation zone, the removal threshold of the biological tissue is not reached.

13. The method of claim 11, wherein the light source is activated such that the second pulse portion is comprised of at least one second pulse and the at least one second pulse has an irradiation intensity that decreases over time.

14. The method of claim 11, further comprising activating the light source such that the second pulse portion is comprised of at least one second pulse and the at least one second pulse initially has an irradiation intensity that increases over time and then subsequently decreases over time.

15. The method of claim 14, wherein the light source is activated such that the second pulse portion comprises a sequence of second pulses and each successive second pulse has a decreasing irradiation intensity but an increasing pulse duration, and for a predetermined size irradiation zone, the energy of each of the second pulses is below the biological tissue removal threshold value.

16. A method for removing biological tissue by irradiation from a light source which is selectively activated for applying its output light to said biological tissue, the method comprising:
controlling the activation of said light source for selectively supplying a sequence of first pulses, each of the first pulses being followed by at least one second pulse;
wherein:
each of the first pulses has an intensity sufficient for removing biological tissue with a small thermal effect in the tissue irradiated;
each second pulse has an intensity not sufficient for removing biological tissue but sufficient to produce a large thermal effect in the tissue irradiated;
the pulses have substantially the same wavelength.

* * * * *